(12) United States Patent
Dai et al.

(10) Patent No.: US 8,110,710 B2
(45) Date of Patent: *Feb. 7, 2012

(54) PROCESS FOR PRODUCING BIS-ALKOXYLATED DIOLS OF BISPHENOL A FROM SPENT POLYCARBONATE DISCS(PC) OR PC WASTE

(75) Inventors: Shenghong A. Dai, Taichung (TW); Chao-Hsing Lin, Taichung (TW); Hsing-Yo Lin, Taichung (TV); Wei-Zhi Liao, Taichung (TW)

(73) Assignee: National Chung-Hsing University, Taichung (TW)

( * ) Notice: Subject to any disclaimer, the term of this patent is extended or adjusted under 35 U.S.C. 154(b) by 426 days.

This patent is subject to a terminal disclaimer.

(21) Appl. No.: 11/978,561

(22) Filed: Oct. 30, 2007

(65) Prior Publication Data

US 2008/0255395 A1    Oct. 16, 2008

(30) Foreign Application Priority Data

Oct. 31, 2006    (TW) ................................ 95140303 A

(51) Int. Cl.
*C07C 43/02*    (2006.01)
*C07C 41/01*    (2006.01)

(52) U.S. Cl. ....................... 568/609; 568/640

(58) Field of Classification Search ........................ None
See application file for complete search history.

(56) References Cited

U.S. PATENT DOCUMENTS

| | | | | |
|---|---|---|---|---|
| 5,077,442 A * | 12/1991 | Hara et al. | ..................... | 568/864 |
| 5,288,923 A * | 2/1994 | Fennhoff et al. | .............. | 568/640 |
| 5,434,290 A * | 7/1995 | Stahl et al. | ..................... | 558/353 |
| 6,603,024 B1 * | 8/2003 | Harada et al. | .................. | 549/434 |
| 6,624,333 B1 * | 9/2003 | Koser et al. | .................... | 568/609 |

OTHER PUBLICATIONS

Oku et al., Chemical conversion of poly(carbonate) to bis(hydroxyethyl) ether of bisphenol A. An approach to the chemical recycling of plastic wastes as monomers, Polymer, issue 41, Aug. 2000, pp. 6749-6753.*

Lin et al., Novel chemical recycling of polycarbonate (PC) waste into bis-hydroxyalkyl ethers of bisphenol A for use as PU raw materials, Green Chemistry, Issue 9, Jan. 2007, pp. 38-43.*

Yoshiteru et al., abstract and computer generated translation of JP 2004-107266, published Apr. 2004.*

Copending U.S. Appl. No. 11/978,560, filed Oct. 30, 2007.*

* cited by examiner

*Primary Examiner* — Rosalynd Keys
(74) *Attorney, Agent, or Firm* — Pai Patent & Trademark Law Firm; Chao-Chang David Pai

(57) ABSTRACT

This invention provides one-pot reaction for digesting polycarbonate waste with alkylene glycol in the presence of a basic catalyst at 180° C. under normal atmospheric pressure. The digested product mixture was found to consist of bisphenol A (BPA) and monoalkoxylated and bisalkoxylated diols of BPA. Alkoxylation of BPA and monoalkoxylated diols of BPA is performed by adding urea or urea derivative (or carbonic acid ester or amine ester) to the digested product mixture at a high temperature under normal atmospheric pressure to obtain the final product, i.e., bisalkoxylated diols of BPA in high yield. The bisalkoxylated diols of BPA may be used as raw materials to synthesize polymer such as polyurethane (PU) or polyester.

20 Claims, 1 Drawing Sheet

PROCESS FOR PRODUCING BIS-ALKOXYLATED DIOLS OF BISPHENOL A FROM SPENT POLYCARBONATE DISCS(PC) OR PC WASTE

FIELD OF THE INVENTION

This invention relates to a process for digesting spent polycarbonate discs or PC waste thereof with alkylene glycols in the presence of a basic catalyst by a one-pot reaction under normal atmospheric pressure. The initial digested product mixture was found to include bisphenol A (BPA) and mono-alkoxylated and bis-alkoxylated diols of BPA. Further, alkoxylation of PC digested product mixture containing BPA, monoalkoxylated and diols of BPA is performed by adding urea (or carbonyl compounds isoelectonic with urea such as carbonic acid ester or amine ester) at about 160° C. under normal atmospheric pressure to obtain the final product, i.e., bis-alkoxylated diols of BPA. The bis-alkoxylated diols of BPA may be used as raw materials to synthesize polymers such as polyurethanes (PU) or polyesters.

BACKGROUND OF THE INVENTION

Currently, spent CD (Compact Disc) substrate is typically made of optical-grade polycarbonate (PC) because of its high-performance chemical properties, such as high transparency, high mechanical strength, low water absorption, low cost and easy to handle when comparing with other substrate materials. Taiwan is one of the biggest producers of compact discs in the world, producing 5.5 billions a year (about 80% of the world market). Defective discs make up about 5-8 percent of production during the manufacturing process, i.e., nearly 600 million discs weighed at least 4,200 metric tons per year. Waste or spent compact discs are typically treated by breaking process, grinding (polishing) process or sandblasting process to separate the metal from plastic parts of the discs. The separated PC resin can be used to blend with other plastic materials or as recycled materials.

For example, the Bayer Group in Germany mainly utilizes the recycled PC in three ways: (1) reselling—15% of the recycled PC is sold to the downstream manufacturers as PC-CD substrate for injection-molding or blending; (2) recycled—65% of the recycled PC is blended with high-molecular-weight PC to form material of certain specification suitable for customers' injection-molding need; (3) plastic composite—20% of the recycled PC is combined with different kinds of plastic to form plastic composite. However, the Bayer recycled PC is only utilized as recycled materials but not regenerated for new uses.

Therefore, the present invention provides a novel process for the chemical recycling of spent PC discs or polycarbonate (PC) waste into bis-alkoxylated diols of bisphenol A, useful polymer intermediates, to meet the industry's requirement and find brand new uses for the spent PCs.

SUMMARY OF THE INVENTION

Therefore, it is an object of the present invention to provide a environment-friendly and economical process for converting spent polycarbonate discs (PC) or waste thereof into bis-alkoxylated diols of bisphenol A capable of being utilized as raw materials to synthesize polymers such as polyurethanes (PU) or polyesters (PE).

The bis-alkoxylated diols of bisphenol A of the present invention has the following formula:

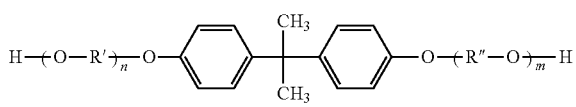

wherein n is an integer of from 1 to 5; m is an integer of from 1 to 5; R' represents C2-C4 alkyl or C2-C4 alkyl substituted with OH, and R" represents C2-C4 alkyl or C2-C4 alkyl substituted with OH.

The R' and R" described above may be [R', R"]=[$CH_2CH_2$, $CH_2CH_2$], [$CH_2CH(CH_3)$, $CH_2CH(CH_3)$], [$CH_2CH(CH_3)$, $CH(CH_3)CH_2$], [$CH_2CH(CH_3)$, $CH_2CH(CH_3)$], [$CH_2CH(CH_2CH_3)$, $CH_2CH(CH_2CH_3)$], [$CH_2CH(CH_2CH_3)$, $CH(CH_2CH_3)CH_2$], [$CH_2CH(CH_3)$, $CH_2CH(CH_2CH_3)$].

According to the present invention, the process for producing bis-alkoxylated diols of bisphenol A may comprise the steps of: (a) digesting polycarbonate (PC) or PC waste with alkylene glycol or mixture of glycols in the presence of a basic catalyst at a temperature of about 100° C. to about 250° C. under normal atmospheric pressure; and (b) forming bis-alkoxylated diols of bisphenol A by adding chemical A to the digested product of step (a) in the presence of a metal oxide catalyst at a temperature of about 100° C. to about 250° C. under normal atmospheric pressure. Chemical A represents urea, a urea derivatives, or any carbonyl compound isoelectonically similar to urea such as the following formula (I), a carbonic acid ester having the following formula (II) or an urethane (carbamate) having the following formula (III):

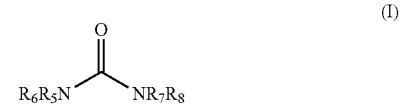

(I)

(II)

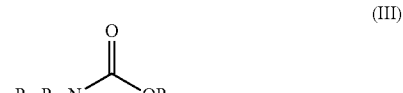

(III)

wherein $R_5$, $R_6$, $R_7$ and $R_8$ each independently represents H or C1-C6 alkyl, $R_9$ and $R_{10}$ each independently represents C1-C6 alkyl, $R_{11}$ and $R_{12}$ each independently represents H or C1-C6 alkyl, and $R_{13}$ represents C1-C6 alkyl. All these groups (R1~13) could also be phenyl or substituted phenyl groups representing aromatic ureas for I, aromatic carbonates for II and aromatic carbamates for III respectively.

The alkylene glycols suitable for use in the step (a) include ethylene glycol, propylene glycol, 1,2-butylene glycol or mixture thereof. The stoichiometric ratio of alkylene glycol to spent polycarbonate (PC) or PC waste may be about 2 to about 100. The basic catalyst is preferably NaOH, KOH, $Na_2CO_3$, $LiCO_3$, $K_2CO_3$, $NaHCO_3$, $KHCO_3$ or t-BuOK. The weight ratio of the basic catalyst to polycarbonate (PC) or PC waste is between 0.001 and 0.5. The reaction temperature of step (a) ranges from about 100° C. to about 250° C. The reaction pressure of step (a) preferably carries out under atmospheric pressure to recover the ammonia and carbon dioxide evolved, but it can also be done under pressure ranging from 1 to 100 atm.

In the step (b), the stoichiometric ratio of urea, carbonate or carbamate to polycarbonate (PC) or PC waste is about 1 to about 20. The metal oxide catalyst may be ZnO, T-12 or MgO. The weight ratio of the metal oxide catalyst to polycarbonate (PC) or PC waste is between 0.001 and 0.5. The reaction pressure of step (b) ranges from 1 to 100 atm. The reaction temperature of step (b) is about 100° C. to about 250° C.

BRIEF DESCRIPTION OF THE DRAWINGS

Other objects, advantages, and novel features of the invention will become more apparent from the following detailed description when taken in conjunction with the accompanying drawing.

DETAILED DESCRIPTION OF THE PREFERRED EMBODIMENT

Figure 1:
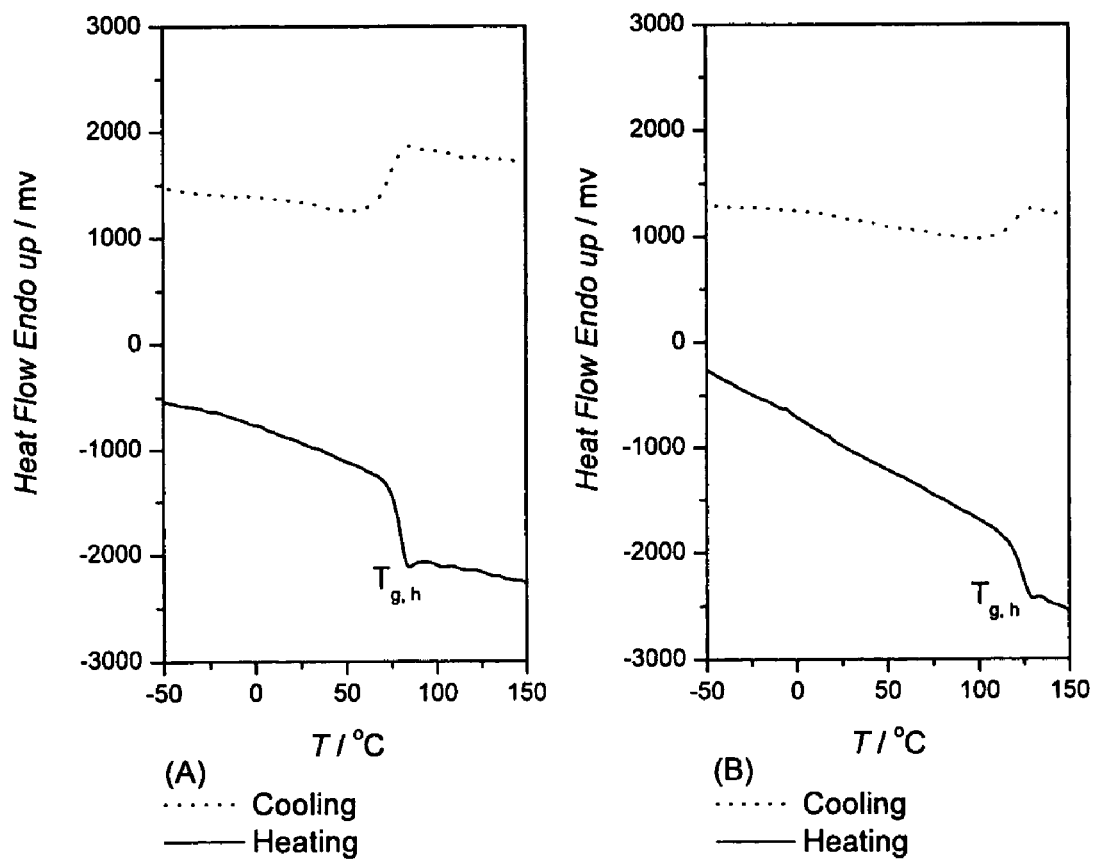
FIG. 1 shows DSC traces (first cooling and second heating traces) of PU polymers of application examples 3 and 4 at a heating/cooling rate of 10° C. min$^{-1}$.

Taking polycarbonate, alkylene glycol, and zinc oxide and sodium carbonate catalyst as an example, the present invention is embodied by the following scheme:

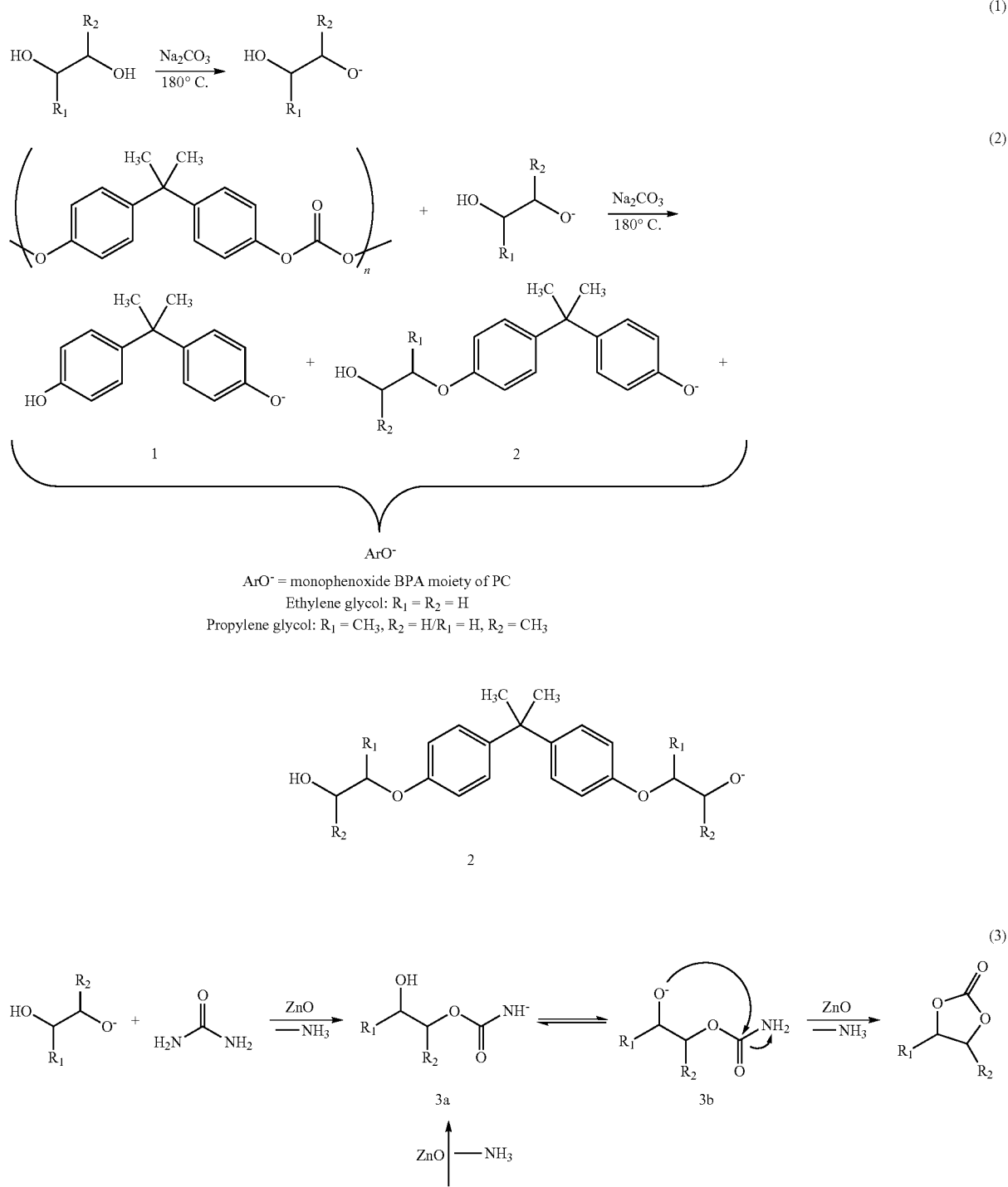

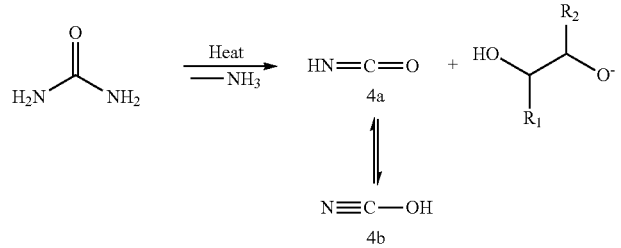

(4)

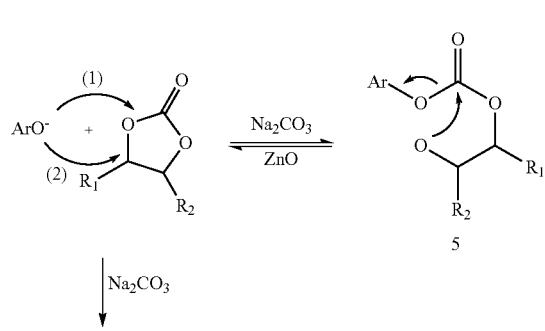

(5)

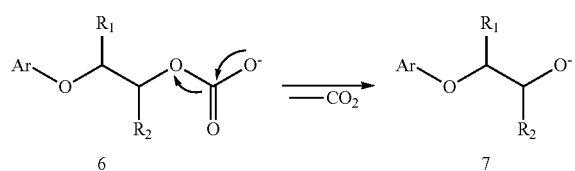

(6)

As shown in Eq. (1), the alkylene glycol forms a negatively alkylene glycoxy anion in the presence of sodium carbonate catalyst at a temperature of 180° C. under normal atmospheric pressure.

As shown in Eq. (2), polycarbonate waste is reacted with the negatively charged alkylene glycoxy anion into formation of bisphenol A (BPA) and monoalkoxylated and bisalkoxylated diols of BPA in the presence of sodium carbonate catalyst at a temperature of 180° C. under normal atmospheric pressure. During the course of reaction, cyclic carbonate was formed in transit and was consumed to generate partial alkoxylated BPA and carbon dioxide as the by-product.

As shown in Eq. (3), cyclic alkylene carbonate is formed also in the subsequent sequence by reacting with the negatively charged alkylene alkoxy anion with urea and zinc oxide catalyst added after the digestion reaction at a temperature of 180° C. under normal atmospheric pressure.

As shown in Eq. (4), cyclic alkylene carbonate may also be formed by reacting the negatively charged alkylene glycoxy anion reacts with isocyanic acid, thermally decomposed product of a small portion of urea, i.e., at a temperature of 180° C.

As shown in Eq. (5) and Eq. (6), bisalkoxylated diols of BPA is formed by ester-exchange reaction between bisphenol A (and monoalkoxylated bisalkoxylated diols of BPA) and alkylene carbonate with concurrent evolution of carbon dioxide.

Several examples are embodied below to show the detailed reaction conditions and results.

Example 1

Preparation of bis-hydroxyethyl Ether of Bisphenol A (BHE-BPA)

To a 500 mL round bottom flask, equipped with a magnetic stirrer, thermometer, and reflux condenser, was charged with waste polycarbonate (50.8 g; 0.2 mol), ethylene glycol (124.0 g; 2.0 mol) and $Na_2CO_3$ (0.4 g) as a catalyst. Then the reaction mixture was heated to 180° C. under atmospheric pressure and was kept at the same temperature for about 20 minutes. Thereafter, the reaction mixture was charged with urea (21.6 g; 0.36 mol) and ZnO (0.2 g) as a catalyst. The mixture was heated at 180° C. under atmospheric pressure for 2 hours, cooled to room temperature, and then filtered out the catalyst. The excess unreacted ethylene glycol (88.4 g; 89% recovery) was removed by vacuum distillation. Toluene (50 mL) was poured into the distillation residue for purification the product by re-crystallization. The white solid was filtered and dried to afford BHE-BPA (63.2 g, 99% yield; Melting point 112-113° C.).

Example 2

Preparation of bishydroxypropyl Ether of Bisphenol A (BHP-BPA)

Repeat the reaction steps of Example 1 wherein reagents, quantities, reaction temperature and time are shown in Table 1. In addition, the final purification step is performed by ethyl acetate extraction.

TABLE 1

| Example | Waste Polycarbonate (mol) | Glycol (mol) | PC Digestion Time (min) | Urea (mol) | Alkoxylation Reaction Time (hour) | Yield (%) |
|---|---|---|---|---|---|---|
| 1 | 0.200 | Ethylene Glycol (2) | 20 | 0.36 | 2 | 99 |
| 2 | 0.118 | Propylene Glycol (12) | 30 | 0.24 | 3 | 91 |

The digestion product of phase I reaction obtained in Example 1 was found to consist of bisphenol A (BPA, 26%), monohydroxyethyl ether of BPA (MHE-BPA, 40%) and bishydroxyethyl ether of BPA (BHE-BPA, 25%) by HPLC analysis. The digestion product of phase I reaction obtained in Example 2 was found to consist of bisphenol A (BPA, 27%), mono-hydroxypropyl ether of BPA (MHP-BPA, 53%) and bis-hydroxypropyl ether of BPA (BHP-BPA, 21%) by HPLC analysis.

Example 3

Preparation of bis-hydroxybisethoxy Ether of Bisphenol A

To a three-neck 500 mL round bottom flask, equipped with a magnetic stirrer, a thermometer, and a reflux condenser, was charged with waste polycarbonate (101.6 g; 0.4 mol/carbonate unit), ethylene glycol (124.2 g; 2.0 mol) and $Na_2CO_3$ (1.5 g) as a catalyst. Then, the reaction mixture was heated to 170° C. under atmospheric pressure with a nitrogen atmosphere until polycarbonate is dissolved to form a clear solution. During the reaction, ethylene glycol is refluxed back to the flask by the reflux condenser.

Thereafter, the reaction mixture was charged with urea (48.08 g; 0.8 mol) and ZnO (1.5 g) as a catalyst. The mixture was heated at 170° C. under atmospheric pressure for 7 hours until bisphenol A (BPA) and mono-hydroxypropyl ether of BPA (MHP-BPA) are completely reacted.

After vacuum distillation at 120° C. under $1.7 \times 10^{-4} \sim 1.95 \times 10^{-4}$ atm, the distillation residue is recovered to afford the desired product (135.38 g, yield) in the flask.

The present invention is characterized by utilizing one-pot reaction to digest polycarbonate with alkylene glycol in the presence of sodium carbonate catalyst and perform alkoxylation reaction in the subsequent step by adding urea and zinc oxide catalyst after the digestion is completed. The advantages of the present invention include:

1. One of the reaction catalysts, zinc oxide, can be easily removed by filtration after the reaction is completed.
2. The excess alkylene glycol serves both as solvent and as a reagent during the reaction process and can be recovered from the reaction product by vacuum distillation after the reaction is completed. The recovered alkylene glycol can be re-used thereby reducing manufacturing cost.
3. Low-cost urea or carbonate was used as reaction material thereby reducing manufacturing cost and increasing market competitiveness.
4. Use waste PC as reaction material thereby making the partial BPA alkoxylated alcohols and then to the final bis-alkoxylated products, reducing manufacturing cost and protecting the environment.
5. The whole reaction can be performed under normal atmospheric pressure without involving highly reactive reagents.
6. If ammonia and carbon dioxide generated in the process could be re-combined into urea again, the whole process becomes even more economical and environmental friendly since water becomes the only by-product in the overall net reaction.

Synthesis of PU

The bis-alkoxylated diols of BPA of the present invention may be used as raw materials to synthesize polymer such as polyurethane (PU) and polyesters.

Application Example 1

Production of Polyurethane (PU) Elastomer from BHE-BPA

BHE-BPA was reacted with methylene diphenylene diisocyanate (MDI) and polytetramethylene-ether-glycol (PT-MEG) as designated in Table 2 to form PU elastomer.

Application Example 2

Production of Polyurethane (PU) Elastomer from BHP-BPA

BHP-BPA was reacted with methylene diphenylene diisocyanate (MDI) and polytetramethylene-ether-glycol (PT-MEG) as designated in Table 2 to form PU elastomer.

Application Example 3

Production of Polyurethane (PU) Plastic from BHE-BPA

BHE-BPA was reacted with methylene diphenylene diisocyanate (MDI) as designated in Table 2 to form PU plastic.

Application Example 4

Production of Polyurethane (PU) Plastic from BHP-BPA

BHP-BPA was reacted with methylene diphenylene diisocyanate (MDI) as designated in Table 2 to form PU plastic.

| APPLICATION EXAMPLE | Molar Ratio |
|---|---|
| 1 | MDI/BHE-BPA/PTMEG 2000 (1/0.8/0.2) |
| 2 | MDI/BHP-BPA/PTMEG 2000 (1/0.8/0.2) |
| 3 | MDI/BHE-BPA (1/1) |
| 4 | MDI/BHP-BPA (1/1) |

Molecular Weight Analysis

The molecular weight of PU polymers of application examples 1-4 were measured by means of GPC with DMF as solvent as shown in Table 3.

Thermal Analysis

PU polymers of application examples 1-4 were measured by means of TGA. The temperatures of 5% mass loss for PU polymers of application examples 1-4 were 291° C., 289° C., 285° C. and 279° C., respectively. DSC was used to obtain characteristics of the thermal transitions of PU polymers. The first cooling and second heating traces of PU polymers of application examples 3 and 4 are shown in FIGS. 1 (A) and (B). The $T_{g,h}$ of PU polymers of application examples 3 and 4 were observed at 81° C. and 123° C., respectively (as shown in Table 3). For PU polymers of application examples 1 and 2, no signs of melting points or crystallization peaks for the hard and soft segments could be discerned. This implies that both PU polymers are amorphous polymers in nature.

TABLE 3

| APPLICATION EXAMPLE | $T_d{}^a$ (° C.) | $T_{g,h}{}^b$ (° C.) |
|---|---|---|
| 1 | 291 | Not Observed |
| 2 | 289 | Not Observed |
| 3 | 285 | 81 |
| 4 | 279 | 123 |

$^a$ Determined at a heating rate of 10° C. min$^{-1}$.
$^b$ Hard segment.

Mechanical Property Analysis

Films of PU polymers of application examples 1 and 2 were cast from their DMF solutions. Hardnesses/shore of films of PU polymers of application examples 1 and 2 are measured to be D43 and A86 as shown in Table 4. 100% Young's modulus, tensile strength and strain at break of films of PU polymers of application examples 1-4 are shown in Table 4. 100% Young's modulus of the film of application example 1 can not be measured. Having a Hardnesses/shore of D43, the film of application example 1 behaves like a plastic, but the film of application example 2 behaves like as an elastomer.

TABLE 4

| APPLICATION EXAMPLE | Hardness (shore) | 100% Young's Modulus (MPa) | Strength (MPa) | Strain at Break (%) | Mw (g mol$^{-1}$) | PDI |
|---|---|---|---|---|---|---|
| 1 | D 43 | — | 10.9 | 48 | 27,590 | 1.8 |
| 2 | A 86 | 6.6 | 15.0 | 340.6 | 64,959 | 3.1 |
| 3 | — | — | — | — | 188,106 | 1.6 |
| 4 | — | — | — | — | 45,870 | 1.8 |

From the thermodynamic and mechanical analysis results listed above, we have shown that PU polymers possessing with unique mechanical properties can be prepared from the bisalkoxylated diols of BPA of the present invention formed by polycarbonate digestion and was followed by alkoxylation to convert all residual phenolic groups into alkoxylated diols.

The present invention utilizes one-pot reaction to perform digestion of polycarbonate (PC) or PC waste and following alkoxylation to form bis-alkoxylated diols of BPA. In the first digestion stage of the present invention, spent polycarbonate discs (PC) or PC waste is digested with excess alkylene glycol in the presence of basic catalyst at a high temperature under normal atmospheric pressure. Alkylene carbonates are generated only in transit during the digestion process, but are quickly consumed to produce the partial alkoxylation products of BPA in the digestion stage. The digestion product gave only approximately 50% of all phenolic alkoxylation products of BPA. In the second alkoxylation stage of the present invention, additional excess urea is added to react with excess alkylene glycol to generate more cyclic alkylene carbonates at a high temperature under normal atmospheric pressure. The cyclic alkylene carbonates generated in the second stage reacts with the un-alkoxylated phenol groups formed in the first stage to achieve a complete alkoxylation. One-pot reaction and low-cost raw materials afford the present invention with advantages of simple process and low manufacturing cost.

What is claimed is:

1. A process for producing bisalkoxylated diols of bisphenol A which comprises the steps of:
    (a) digesting polycarbonate (PC) or PC waste with alkylene glycol in the presence of a basic catalyst at a temperature of about 100° C. to about 250° C. under normal atmospheric pressure; and
    (b) forming bisalkoxylated diols of bisphenol A by adding chemical A to the digested product of step (a) in the presence of a metal oxide catalyst at a temperature of about 100° C. to about 250° C. under normal atmospheric pressure, wherein chemical A represents an amine ester having the following formula (III):

(III)

wherein $R_{11}$ and $R_{12}$ each independently represents H or $C_1$-$C_6$ alkyl, and $R_{13}$ represents $C_1$-$C_6$ alkyl.

2. The process according to claim 1, wherein alkylene glycol is selected from the group consisting of ethylene glycol, propylene glycol, 1,4-butylene glycol, 1,3-butylene glycol, glycerol and a mixture thereof.

3. The process according to claim 1, wherein stoichiometric ratio of alkylene glycol to polycarbonate (PC) or PC waste is about 2 to about 100.

4. The process according to claim 1, wherein the basic catalyst is selected from the group consisting of NaOH, KOH, $Na_2CO_3$, $LiCO_3$, $K_2CO_3$, $NaHCO_3$, $KHCO_3$ and t-BuOK.

5. The process according to claim 1, wherein the weight ratio of the basic catalyst to polycarbonate (PC) or PC waste is between 0.001 and 0.5.

6. The process according to claim 1, wherein the reaction pressure of step (a) ranges from 1 to 100 atm.

7. The process according to claim 1, wherein stoichiometric ratio of amine ester to polycarbonate (PC) or PC waste is about 1 to about 20.

8. The process according to claim 1, wherein the metal oxide catalyst is ZnO or MgO.

9. The process according to claim 1, wherein the weight ratio of the metal oxide catalyst to polycarbonate (PC) or PC waste is between 0.001 and 0.5.

10. The process according to claim 1, wherein the reaction pressure of step (b) ranges from 1 to 100 atm.

11. A process for producing bisalkoxylated diols of bisphenol A which comprises the steps of:
    (a) digesting polycarbonate (PC) or PC waste with alkylene glycol in the presence of a basic catalyst at a temperature of about 100° C. to about 250° C. under normal atmospheric pressure; and
    (b) forming bisalkoxylated diols of bisphenol A by adding chemical A to the digested product of step (a) in the presence of a metal oxide catalyst at a temperature of about 100° C. to about 250° C. under normal atmospheric pressure, wherein chemical A represents urea or a carbonyl compound iso-electronic with urea having the following formula (I) or an amine ester having the following formula (III):

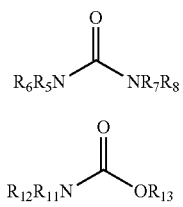

(I)

(III)

wherein $R_5$, $R_6$, $R_7$ and $R_8$ each independently represents H or $C_1$-$C_6$ alkyl, $R_{11}$ and $R_{12}$ each independently represents H or $C_1$-$C_6$ alkyl, and $R_{13}$ represents $C_1$-$C_6$ alkyl.

12. The process according to claim 11, wherein alkylene glycol is selected from the group consisting of ethylene glycol, propylene glycol, 1,4-butylene glycol, 1,3-butylene glycol, glycerol and a mixture thereof.

13. The process according to claim 11, wherein stoichiometric ratio of alkylene glycol to polycarbonate (PC) or PC waste is about 2 to about 100.

14. The process according to claim 11, wherein the basic catalyst is selected from the group consisting of NaOH, KOH, $Na_2CO_3$, $LiCO_3$, $K_2CO_3$, $NaHCO_3$, $KHCO_3$ and t-BuOK.

15. The process according to claim 11, wherein the weight ratio of the basic catalyst to polycarbonate (PC) or PC waste is between 0.001 and 0.5.

16. The process according to claim 11, wherein the reaction pressure of step (a) ranges from 1 to 100 atm.

17. The process according to claim 11, wherein stoichiometric ratio of urea or amine ester to polycarbonate (PC) or PC waste is about 1 to about 20.

18. The process according to claim 11, wherein the metal oxide catalyst is ZnO or MgO.

19. The process according to claim 11, wherein the weight ratio of the metal oxide catalyst to polycarbonate (PC) or PC waste is between 0.001 and 0.5.

20. The process according to claim 11, wherein the reaction pressure of step (b) ranges from 1 to 100 atm.

* * * * *